United States Patent [19]

Yoshida et al.

[11] 4,391,912
[45] Jul. 5, 1983

[54] CELL CULTIVATION METHOD AND FLOATING ANIMAL CELL CULTURE UNIT FOR THE SAME

[75] Inventors: Koichi Yoshida, Fuji; Fusakazu Hayano, Chigasaki, both of Japan

[73] Assignee: Asahi Kasei Kogyo Kabushiki Kaisha, Osaka, Japan

[21] Appl. No.: 188,416

[22] Filed: Sep. 18, 1980

[30] Foreign Application Priority Data

Sep. 18, 1979 [JP] Japan ................. 54/118833

[51] Int. Cl.³ .................. C12N 5/02; C12M 3/00
[52] U.S. Cl. .................. 435/241; 435/284
[58] Field of Search ............ 435/240, 241, 284, 285, 435/286, 287; 210/321.1, 638, 645, 500.2

[56] References Cited

U.S. PATENT DOCUMENTS

| | | | |
|---|---|---|---|
| 3,734,851 | 5/1973 | Matsumura | 210/646 |
| 3,821,087 | 6/1974 | Knazek et al. | 435/285 |
| 3,883,393 | 5/1975 | Knazek et al. | 435/240 |
| 3,911,140 | 10/1975 | Osborne et al. | 435/139 |
| 4,087,327 | 5/1978 | Feder et al. | 435/240 |
| 4,201,845 | 5/1980 | Feder et al. | 435/285 |
| 4,242,460 | 12/1980 | Chick et al. | 435/284 |

FOREIGN PATENT DOCUMENTS 1506785 4/1978 United Kingdom .

OTHER PUBLICATIONS

Ham, Richard G. et al., "Media and Growth Requirements"; *Methods in Enzymology*, Jakoby, W. R. et al., eds., vol. 58, 'Cell Culture'; Academic Press, 1979; pp. 44–49, 81 and 82.

*Primary Examiner*—Raymond N. Jones
*Assistant Examiner*—Elizabeth J. Curtin
*Attorney, Agent, or Firm*—Sughrue, Mion, Zinn, Macpeak & Seas

[57] ABSTRACT

A method of cultivating floating animal cells, such as lymphocytic cells, medullary tumor cells, medullary tumor cells obtained by the cell fusion with other cells, lymphoma cells, leukemic cells, leukocytic cells, mastocarcinoma cells, liver cancer cells, etc., which comprises introducing a culture medium in a cell culture unit comprising a shell and a plurality of hollow fibers enclosed in the shell, said hollow fiber being open at either end outside of the shell and having a pore diameter of from about 20 Å to $10^5$ Å, wherein the culture medium passes through the interior of the hollow fibers and the floating animal cells are cultivated in the space between the shell and the hollow fibers is disclosed. A floating animal cell culture unit for the method is also disclosed.

10 Claims, 8 Drawing Figures

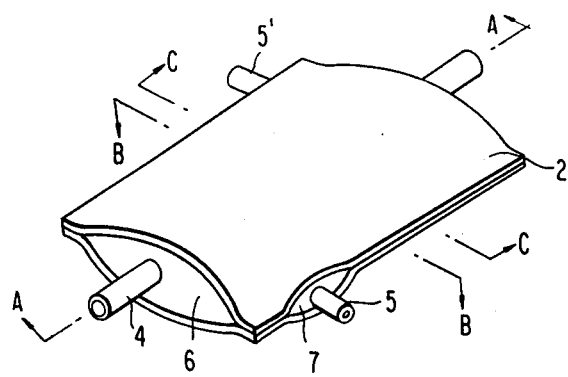
FIG.1
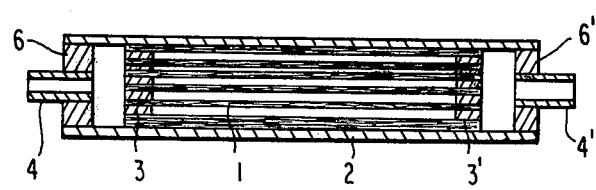
FIG.2
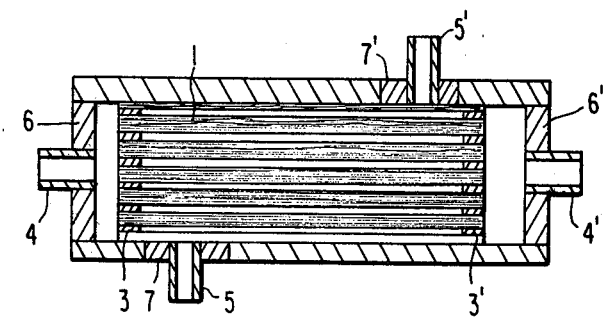
FIG.3
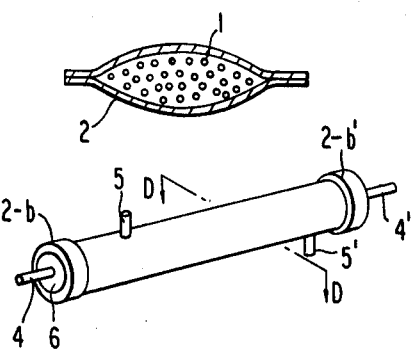
FIG.4
FIG.5
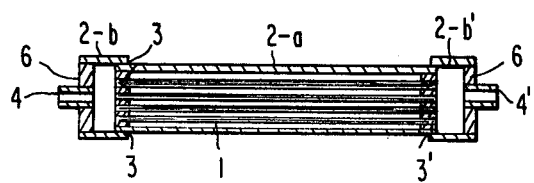
FIG.6

CELL CULTIVATION METHOD AND FLOATING ANIMAL CELL CULTURE UNIT FOR THE SAME

BACKGROUND OF THE INVENTION

1. Field of the Invention

This invention relates to a method for cultivating floating animal cells in a cell culture unit composed of hollow fibers. More particularly it is concerned with a method for cultivating floating animal cells in a cell culture unit composed of a shell and open ended hollow fibers enclosed in the shell, comprising introducing a culture medium through the hollow fibers and cultivating the floating animal cells in the space between the shell and the hollow fibers. The present invention also relates to a floating animal cell culture unit used for the method.

2. Description of the Prior Art

Various methods for cultivating animal cells have been known. Animal cells include those which grow and proliferate while attached to a growth surface (referred to as "attaching cells") and those which grow and proliferate in a floating state (referred to as "floating cells"). Significant advances have been made in the study of cultivation of attaching cells.

Such attaching cells can generally grow and proliferate only in a single layer on the attached surface. Richard A. Knazek, et al., however, have succeeded in three-dimensionally growing and proliferating attaching cells by employing a method in which the attaching cells are grown on the exterior surface of semipermeable hollow fibers or capillaries and a culture medium is passed through the hollow fibers or capillaries (see *Journal of Medicine*, Vol. 296, No. 3, pp. 154–159 (1977)). Additionally, U.S. Pat. No. 3,997,396 discloses a method of three-dimensionally growing and proliferating attaching cells in which the attaching cells are grown on one surface of a hollow fiber membrane and oxygen is supplied to the other surface.

Floating cells are generally weak as compared with attaching cells (see Shoichi Oboshi et al., *Jingansaibo no Baiyo*, Asakura Shoten, Tokyo, page 44 (1975)). It has therefore been considered difficult to grow and proliferate the floating cells in desired high densities. Such considerations have led to the conclusion that all of the above-described methods using hollow fibers are limited to the cultivation of the attaching cells.

Methods which are generally used in the cultivation of floating cells include a stationary floating culture method and a suspension culture method using agitation, rotary stirring, or the like. These methods, however, have disadvantages, in that: (1) large scale equipment is required, since it is difficult to grow and proliferate the cells in high densities; (2) difficulties are encountered in separating the cells from nutrients, metabolic products, wastes, etc.; (3) it is difficult to continuously exchange the culture medium; and (4) the possibility of being contaminated by other microorganisms is great. It has, therefore, been greatly desired to remove these disadvantages, in particular, on the ground that the floating cells produce metabolic products which are of importance from the medical and veterinary standpoint, e.g., diagnosis and medical treatment of various diseases.

As described above, the progress in the method of growing and proliferating attaching animal cells is remarkable, and it has now become possible to grow and proliferate the attaching animal cells three-dimensionally, i.e., like a tissue, by using hollow fibers. On the other hand, the cultivation of the floating cells has been carried out by the conventional methods as described above. According to these methods, it is difficult to grow and proliferate floating cells in high densities. Therefore, various problems are involved in producing useful metabolic products from the floating cells by the cultivation thereof in large amounts.

SUMMARY OF THE INVENTION

An object of this invention is to provide a cultivation method which enables the growth and proliferation of floating animal cells both in high density and continuously.

Another object of this invention is to provide a cell culture unit effective for the cultivation of floating animal cells.

It has now been discovered that when floating animal cells are cultured, in a cell culture unit comprising a shell and open ended hollow fibers enclosed in the shell in the space between the shell and the hollow fibers, by flowing a culture medium through the interior of the hollow fibers, the floating cells grow and proliferate in high densities. It has also been found that while it is generally desirable that the pore diameters of the hollow fibers be within a range of from about 20 Å to $10^5$ Å, when the hollow fibers have pore diameters falling in the range of from $10^2$ Å to $5 \times 10^4$ Å, the floating cells grow and proliferate in even higher densities.

The reason for this is believed to be that under the conditions described the exchange of the nutrients in the culture medium and the metabolic products and wastes in the cells proceeds very smoothly, producing an environment favorable for the growth and proliferation of the cells.

It has also been found that the method of this invention is applicable generally to floating animal cells, and that the method produces good results in the proliferation of floating cells obtained by cell fusion with other cells.

BRIEF DESCRIPTION OF THE DRAWINGS

FIG. 1 is a perspective view of cell culture unit useful in the practice of this invention;

FIG. 2 is a cross sectional view taken along line A—A of FIG. 1;

FIG. 3 is a cross sectional view taken along line B—B of FIG. 1;

FIG. 4 is a cross sectional view taken along line C—C of FIG. 1;

FIG. 5 is a perspective view of another embodiment of a cell culture unit useful in the practice of this invention;

FIG. 6 is a cross sectional view, taken along line D—D, of FIG. 5;

DETAILED DESCRIPTION OF THE INVENTION

Figure 7:
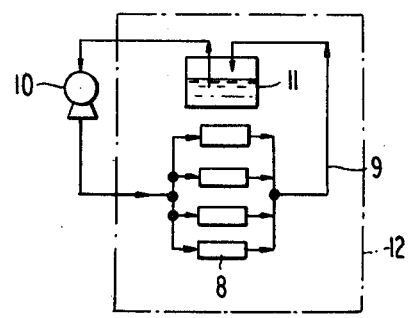
FIG. 7 is a diagram illustrating a cell culture apparatus utilizing cell culture units according to this invention.

This invention provides a cultivation method of floating animal cells which utilizes a cell culture unit comprising a shell and open ended hollow fibers having pore diameters of from 20 Å to $10^5$ Å enclosed in the shell, with both ends of said hollow fiber being open to the outside of the shell, by flowing a culture medium through the interior of the hollow fibers, with the floating animal cells being grown in the space between the shell and the hollow fibers.

First, cell culture units and apparatus useful in the practice of the method of this invention will be explained.

The structure of the cell culture unit is not particularly limited provided that the hollow fibers have pore diameters of from 20 Å to $10^5$ Å, are enclosed in the shell, and both ends of the hollow fibers are open to the outside of the shell.

Suitable examples are explained with reference to the accompanying drawings.

FIGS. 1 to 4 illustrate an embodiment of a cell culture unit according to the invention in which a plurality of hollow fibers 1 are enclosed in a shell 2 which is obtained by bonding together two sheets in a bag-form. The hollow fibers 1 are held in place at either side by fixing layers 3 and 3', and the interiors of the hollow fibers 1 are open to the outside. Tubes 4 and 4' communicating with the interiors of the hollow fibers 1 are open to the outside of the shell. A culture medium can be introduced and withdrawn through tubes 4 and 4'. Additionally, tubes 5 and 5' are provided which communicates with the space defined between the hollow fibers 1 and the shell 2 and which is open to the outside of the shell. Through these tubes 5 and 5' the floating cells can be introduced and withdrawn. Side walls 6 and 6' seal both ends of the shell 2 and simultaneously hold in place the tubes 4 and 4'. Walls 7 and 7' hold the tubes 5 and 5' in place and seal the boundary of the tubes 5 and 5'.

FIGS. 5 and 6 illustrate another embodiment in which a shell is formed by providing connection members 2-b and 2-b' having tubes 4 and 4' at both ends of a pipe 2-a accomodating a plurality of hollow fibers 1. These hollow fibers 1 are held in place at each end by fixing layers 3 and 3' in the same manner as described above, and tubes 5 and 5' through which the floating cells are introduced and withdrawn are provided at side walls of the pipe 2-a. A wide tube can be used as the pipe 2-a. The internal diameter of the tube is not limited but generally from about 5 mm to about 10 cm.

In the above embodiments, if the shell is made of a soft material, the tubes 5 and 5' need not be provided, because the floating cells can be introduced and withdrawn by use of a syringe.

The cell culture units as described above can be incorporated in a culturing apparatus as illustrated in FIG. 7, wherein both open ends of the hollow fibers in, e.g., cell culture unit 8, are connected through a pump 10 to a culture medium reservoir 11 by use of a tube 9 made of a material having excellent gas permeability. The entire apparatus, or the apparatus except for the pump 10, is placed in a carbon dioxide gas incubator 12, and the cultivation is carried out at a constant temperature.

Hereinafter, the parts for use in the cell culture unit and apparatus will be explained in more detail.

Hollow fibers may be made of any semipermeable substance which exerts no adverse influences on the floating cells. Suitable examples of such substances are polysulfone, polyether sulfone, polyacrylonitrile, cellulose acetate, polycarbonate, polymethyl methacrylate, cuprammonium cellulose and the like. Among these substances, polysulfone and polyether sulfone are preferred because, as is described below and shown in the examples, they permit the growth and proliferation of floating cells in high densities and can be steam-sterilized.

In order to increase the proliferation rate of the floating cells, it is necessary to promptly and continuously supply large amounts of nutrients and oxygen and remove cellular wastes. For attaining the prompt and continuous supply and removal, diameters of pores present in the walls of the hollow fibers should be at least be 20 Å. The reason for this is believed to be that giant molecules necessary for the proliferation of the floating cells, such as proteins and nucleic acids, are required to be supplied from the side of the culture medium reservoir. However, when the diameters of pores present in the walls of the hollow fibers exceeds $10^5$ Å, the floating cells pass through the pores, and the invention cannot be carried out. Detailed investigations have revealed that as the diameters of pores present in the walls of the hollow fibers are greater and the permeation rate of substances is higher, the proliferation rate of the floating cells is not always necessarily higher, and that the pore diameter suitable for maximizing the proliferation and for maintenance varies depending upon the type of the floating cells. In general, the optimum pore diameter is from $10^2$ Å to $5 \times 10^4$ Å. Of course, in this case, pores having diameters of less than $10^2$ Å and pores having diameters of more than $5 \times 10^4$ Å may coexist therewith, provided that the diameters are less than $10^5$ Å.

The hollow fibers used in the present invention can easily be produced according to U.S. Pat. Nos. 3,871,950, 3,888,771 and 3,896,061 and British Pat. Nos. 1,506,785 and 1,565,113.

The fixing layer may be made of any material which does not damage the floating cells and is not deteriorated during a sterilization step. In particular, a silicone polymer adhesive is preferred.

Various materials can be used for forming the shell, any ones exerting no bad influences onto the floating cells can be used. Examples of such materials include glass, polycarbonate, polystyrene, silicone polymer, polysulfone, polyethylene, polyurethane, etc. For supplying sufficient amounts of oxygen to proliferating cells, however, materials having excellent gas permeability are preferred, such as a thin silicone polymer film or tube, a thin silicone polymer film reinforced by a polyester mesh, a thin polybutadiene film or tube, a thin silicone-polycarbonate copolymer film or tube, a porous teflon film, a porous polypropylene film, etc. are preferred. The thickness of the film or tube is preferably from 0.05 to 3 mm.

As a material for forming the tubes for the introduction and withdrawal of the culture medium and floating cells, the same materials as those used for the shell can be used.

The tube for use in connecting the cell culture unit to the culture medium reservoir is also desirably made of a material having excellent gas permeability. Examples of such material include a silicone polymer, polybutadiene, a silicone-polycarbonate copolymer, etc. While the culture medium is being passed through the tube, oxygen is supplied thereto through the tube.

Cells that can be cultured by the method of this invention are subject to no limitations provided that they are floating cells. Examples of such floating cells are described in detail by Junnosuke Nakai et al., *Soshiki*

*Baiyo*, Asakura Shoten, Tokyo, pp. 265-275 (1970) and Shoichi Oboshi et al., *Jingansaibo no Baiyo*, Asakura Shoten, Tokyo (1975). Typical examples of floating cells are lymphocytic cells, medullary tumor cells, lymphoma cells, leukemic cells, mastocarcinoma cells, liver cancer cells, leukocytic cells, etc. The method of this invention is markedly effective for the proliferation of medullary tumor cells, leukemic cells and lymphocytic cells, and it is also markedly effective for the proliferation of floating cells obtained by the cell fusion of medullary tumor cells and other cells such as spleen cells, lymphocytic cells and the like.

The cultivation operation of this invention can be carried out in the following sequence, although it is not limited thereto.

First, the cell culture unit, tubes and culture medium reservoir are sterilized, separately or when in the state that they are all connected together. For this sterilization, steam sterilization, gas sterilization, radiation sterilization, formalin sterilization, etc. can be employed. In particular, the steam sterilization is preferred, because the operation is simple and a post-treatment is not necessary after the sterilization. Since the polysulfone and polyether sulfone can be steam-sterilized, they can advantageously be used as a material for the hollow fibers. In the case of the gas sterilization, formalin sterilization, etc., it is necessary to fully wash the residual gas, formalin, etc. from the apparatus after the sterilization by repeatedly flowing culture medium through the culture apparatus.

After the sterilization, the floating cells can be implanted in the space between the hollow fibers and the shell by use of a syringe. As the floating cells, those suspended in a culture medium are usually employed. The cell density of the suspension for implantation is preferably from $10^5$ to $5 \times 10^6$ cells/ml, although it may vary depending upon the type of cell.

After the implant was completed, the entire culture apparatus, or the apparatus except for the pump, is placed in the carbon dioxide gas incubator into which mixed gases of air-$CO_2$ or $O_2$-$CO_2$ are supplied. The $CO_2$ concentration is preferably from 5 to 10% by weight. The temperature in the incubator is adjusted to about from 35° to 38° C. and the interior of the incubator is always kept in a sufficiently wet state so as to prevent water from being excessively removed from the perfusate.

The method of this invention has a number of advantages over the prior art methods.

According to the method of this invention, the proliferation rate of the floating cells is high, and they can be grown in higher densities than in the suspension method. In general, the floating cells are so weak, in contrast to the attaching cells that it is difficult to cultivate in high cell density. It is believed that when the cell density increases, the mutual action among the cells becomes strong, making it difficult for them to maintain their lives. Thus it is presumed that the cultivation method of this invention permits the continuous and rapid supply of nutrients and oxygen and the continuous and rapid removal of cellular wastes through the hollow fibers, as a result of which the circumstances sufficiently suitable for the cells to overcome the adverse effects of the mutual action among the cells is produced.

Therefore, the cultivation method of this invention permits the minimization of apparatus size in the cultivation of large amounts of floating cells. Furthermore, because of the semipermeability of the hollow fibers, a culture medium containing a metabolic product produced by the floating cells in relatively high purity can easily be separated from the cells, for example, a culture medium containing antibodies or $\alpha$-Fetoprotein can easily be separated from medullary tumor cells or liver cancer cells, respectively, using the floating animal cell culture unit of the present invention. The metabolic product can be separated from the thus obtained culture medium in a conventional manner. For example, $\alpha$-Fetoprotein can be purified by salting out the culture medium separated from liver cancer cells against ammonium sulfate fractionation, dialyzing with a buffer solution and developing by an ion exchange chromatography. In particular, the technique of producing specific antibodies by the cell fusion of the medullary tumor cells and various antibody-producing cells has recently advanced (see *European Journal of Immunology* Vol. 6, pp. 511-519 (1976)). The method of this invention is suitable for the cultivation of hybrid cells producing specific antibodies obtained by such cell fusion, and it enables the production of various high purity antibodies in large quantities. Thus, the medical and veterinary value of this invention is significant.

Furthermore, in the prior art methods, it is necessary to separate the cells from the culture medium in order to periodically exchange the culture medium. On the other hand, in the method of this invention, such separation is not necessary and the culture medium can be continuously supplied. This is a great advantage in achieving practical mass cultivation.

Additionally, in the suspension cultivation method, the possibility of being contaminated by microorganisms such as bacterium and mold is markedly great, and considerable attention should be paid in the cultivation over long periods of time. On the other hand, in the method of this invention, once the floating cells are aseptically implanted, microorganisms can not pass through the walls of the hollow fibers and do not mix with the floating cells. Therefore, aseptic conditions can easily be maintained over long periods of time. Similarly, even if the culture medium is contaminated by microorganisms, the floating cells will not be contaminated by the microorganisms.

The following examples are given to illustrate this invention in greater detail.

EXAMPLE 1

Six kinds of polysulfone hollow fibers having an internal diameter of 250$\mu$, an external diameter of 350$\mu$, and pore diameters of 18 Å, 30 Å, 50 Å, $10^2$ Å, $2 \times 10^2$ Å, and $5 \times 10^2$ Å, respectively, were produced by dissolving an aromatic polysulfone in a mixture solution of N-methylpyrrolidone (solvent), dimethyl sulfoxide (non-solvent), water and sodium nitrate and extruding into water (coagulating liquid) through a hollow-shaped nozzle. Then 100 of each of the polysulfone hollow fibers were inserted in a silicone polymer tube having an internal diameter of 1 cm, an external diameter of 1.3 cm and a length of 8 cm, and both ends of the silicone tube were sealed together with the bundle of the hollow fibers by use of a silicone polymer adhesive. When the silicone polymer adhesive hardened, the silicone tubes were cut at the terminals thereof, to thereby produce cell culture units with a silicone fixing layer and open-ended hollow fibers. Then 50 cm long silicone polymer tubes (internal diameter 3 mm, external diameter 5 mm) were connected to both ends of the above produced cell culture units by use of connection members. These silicone polymer tubes were connected through a pump to a 200 ml culture medium reservoir made of silicone polymer to, thereby produce cell culture apparatus.

After the steam sterilization of the above produced cell culture apparatus, 100 ml of a culture medium (consisting of 80% of a Dulbecco's modified Eagle culture medium and 20% of horse serum) was introduced into the culture medium reservoir and circulated through the interiors of the hollow fibers by the pump. The total amount of a solution prepared by suspending $1.08 \times 10^6$ mouse medullary tumor cells (MPC-11) in 1 ml of the same culture medium as used above was implanted, by use of a syringe, in the space between the hollow fibers and the shell.

The apparatus, excluding the pump, was placed in an isothermic chamber maintained at 38° C., and about 200 to 300 ml/min(per 0.03 m² chamber) of a mixed gas consisting of 95% of air and 5% of $CO_2$ was supplied into the isothermic chamber. Samples were taken over a period of time and the number of proliferated cells was determined. The results are shown in Table 1. In this case, at the 7th and 15th days, the culture medium was exchanged.

TABLE 1

| Pore Diameter of Hollow Fibers (Å) | Number of Implanted Cells | 9th day | 18th day |
| --- | --- | --- | --- |
| 18 (comparison) | $1.08 \times 10^6$ | $1.20 \times 10^6$ | $1.20 \times 10^6$ |
| 30 | " | $1.35 \times 10^7$ | $0.81 \times 10^8$ |
| 50 | " | $3.00 \times 10^7$ | $1.23 \times 10^8$ |
| $10^2$ | " | $4.20 \times 10^7$ | $1.75 \times 10^8$ |
| $2 \times 10^2$ | " | $5.00 \times 10^7$ | $1.90 \times 10^8$ |
| $5 \times 10^2$ | " | $5.70 \times 10^7$ | $2.10 \times 10^8$ |

EXAMPLE 2

In this example, three kinds of cellulose acetate hollow fibers having an internal diameter of 250μ, an external diameter of 350μ and pore diameters of $10^2$ Å, $2 \times 10^3$ Å, $5 \times 10^4$ Å, respectively, were used. 30 of each of the above hollow fibers were inserted in three silicone polymer tubes, respectively, each having an internal diameter of 1 cm, an external diameter of 1.3 cm and a length of 8 cm, and cell culture apparatus was produced in the same manner as in Example 1.

Only the cell culture unit was sterilized with ethyleneoxide gas for 5 hours and the other parts were steam-sterilized. After the sterilization, 100 ml of the same culture medium as was used in Example 1 was circulated through the apparatus, and exchanged for a fresh batch of culture medium once a day. This procedure was repeated for three days to remove the residual ethyleneoxide.

Next, mouse medullary tumor cells (MPC-11) were inoculated and grown in the same manner as in Example 1. Samples were taken over a period of time, and the number of proliferated cells was counted with a microscope. The results are shown in Table 2.

TABLE 2

| Pore Diameter of Hollow Fibers (Å) | Number of Implanted Cells | 9th day | 18th day |
| --- | --- | --- | --- |
| $10^2$ | $1.00 \times 10^6$ | $3.50 \times 10^7$ | $1.50 \times 10^8$ |
| $2 \times 10^3$ | " | $4.75 \times 10^7$ | $2.00 \times 10^8$ |
| $5 \times 10^4$ | " | $3.00 \times 10^7$ | $1.40 \times 10^8$ |

[At the 7th and 15th days, the culture medium was exchanged.]

Figure 8:
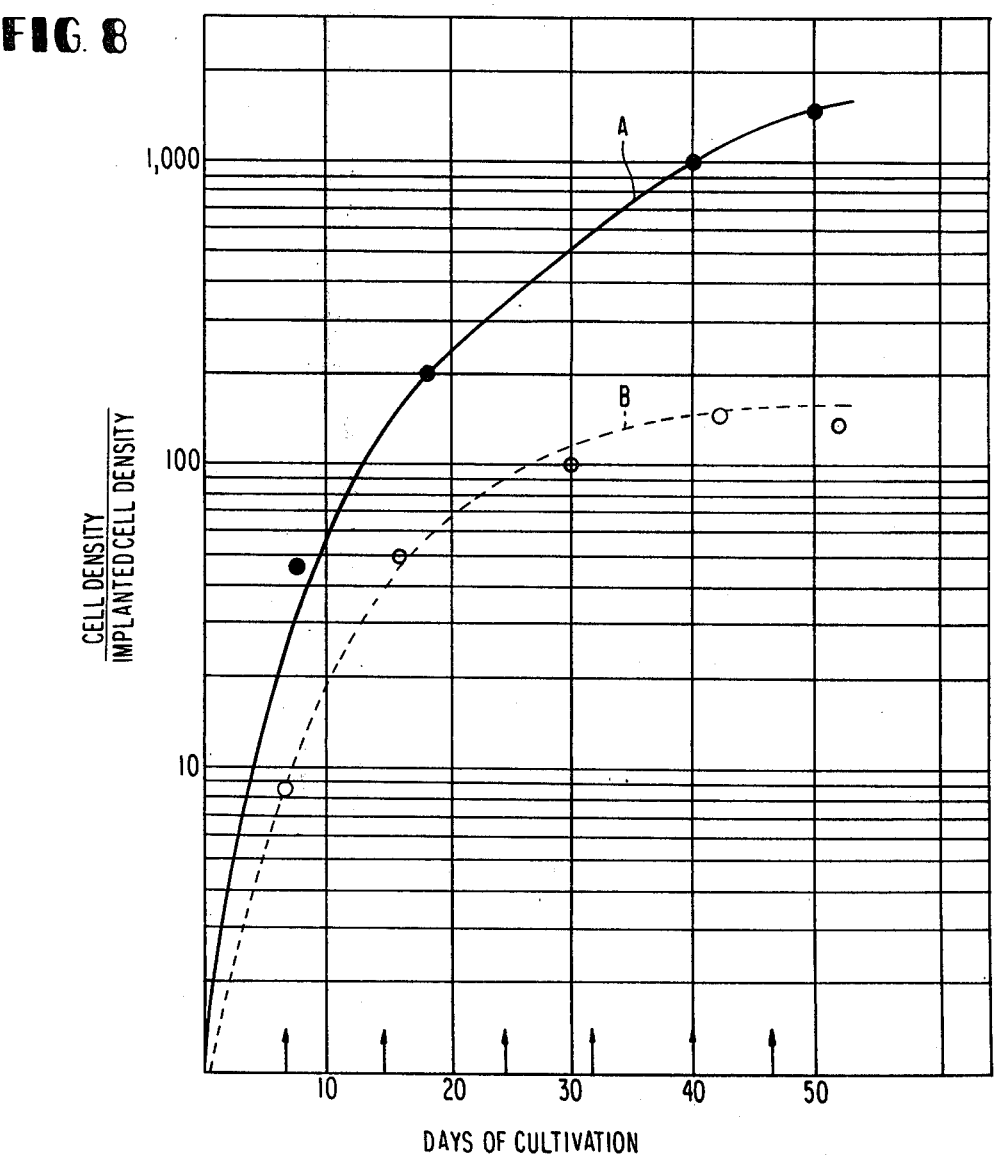
FIG. 8 is a graph showing the difference in cell density between the method of this invention and a prior art method.

For comparison, the same cells as used above were grown using the same culture medium as used above by a suspension method. As this suspension method, the 100 ml scale tapping method was employed. The results are shown in FIG. 8, in which A indicates the cultivation results using the culture unit composed of the hollow fibers having a pore diameter of $2 \times 10^3$ Å, and B indicates the results using the suspension method. The arrow ↑ in FIG. 8 indicates that the culture medium was exchanged.

EXAMPLE 3

By using 30 cellulose acetate hollow fibers having an internal diameter of 250μ, an external diameter of 350μ and a pore diameter of $2 \times 10^3$ Å, a cell culture apparatus was produced in the same manner as in Example 1.

According to the method disclosed by Millstein et al. (*European Journal of Immunology*, Vol. 6, pp. 511–519 (1976)), sheep erythrocyte antibodies were obtained by the cell fusion of mouse medullary tumor cells (MPC-11) and mouse spleen cells immunized by sheep erythrocyte.

$10^6$ of these cells were suspended in 1 ml of the culture medium, implanted in the above cell culture unit and grown therein under the same conditions as in Example 1.

For comparison, the cells were cultured by the same suspension method as in Example 2.

The changes in the number of cells over a period of time were examined, and the results obtained are shown in Table 3.

TABLE 3

| Cultivation Method | Number of Implanted Cells | 9th day | 18th day |
| --- | --- | --- | --- |
| Cell culture unit composed of hollow fibers | $10^6$ | $4.50 \times 10^7$ | $2.2 \times 10^8$ |
| Suspension method (10 ml) (tapping method) | $10^6$/ml | $2.10 \times 10^7$/ml | $8.0 \times 10^7$/ml |

EXAMPLE 4

By using various hollow fibers, cell culture apparatus were produced in the same manner as in Example 1. Burkitt's lymphoma cells of human leukemic cells and mouse medullary tumor cells were implanted in the cell culture apparatus and grown in the same manner as in Example 1. The results are shown in Table 4.

TABLE 4

| Type of Cells | Material for Hollow Fibers | Internal Diameter/ External Diameter (μ) | Pore Diameter (Å) | Number of Cells Implant | 18th day |
| --- | --- | --- | --- | --- | --- |
| lymphoma cells of human | polycarbonate | 200/250 | 25 | $2.00 \times 10^6$ | $5.00 \times 10^6$ |
| | cellulose acetate | 200/250 | $10^3$ | " | $1.20 \times 10^8$ |

TABLE 4-continued

| Type of Cells | Material for Hollow Fibers | Internal Diameter/ External Diameter ($\mu$) | Pore Diameter (A) | Number of Cells Implant | Number of Cells 18th day |
|---|---|---|---|---|---|
| leukemic cells | polyacrylonitrile | 250/350 | 50 | " | $7.00 \times 10^7$ |
| mouse medullary tumor cells | polymethyl methacrylate | 250/350 | 40 | " | $2.50 \times 10^7$ |
| | polycarbonate | 200/250 | 25 | " | $7.00 \times 10^6$ |
| | polyether sulfone | 250/350 | 40 | " | $1.10 \times 10^8$ |

EXAMPLE 5

Peripheral lymphocyte taken from human (see Leslie Hudson and Frank C. Hay, *Practical Immunology*, Blackwell Scientific Publications pp. 17–18) were suspended in a culture medium RPMI 1640 (containing 20% of cow embryo serum) so that the cell density be 10/ml and $5 \times 10^6$/ml. In the same manner as in Example 1, they were implanted in the same cell culture apparatus as used in Example 2. After one week, the cells were taken out from the apparatus, and the activity of the lymphocyte was measured by the pigment excluding test (ibid. pp. 30–32) using Trypan Blue and compared with that prior to the implant. At the same time, the procedure was repeated by the stationary floating culture method, and the results are shown in Table 5.

TABLE 5

| | Residual Activity at 7th Day (%) | |
|---|---|---|
| Method | Number of Implanted Cells ($10^6$/ml) | Number of Implanted Cells ($5 \times 10^6$/ml) |
| Cultivation using Hollow Fibers | 80 | 75 |
| Stationary Floating Culture | 60 | 0 |

$$\text{Residual activity at 7th day} = \frac{\text{Pigment excluding capability at 7th day}}{\text{Pigment excluding capability prior to implant}} \times 100$$

While the invention has been described in detail and with reference to specific embodiments thereof, it will be apparent to one skilled in the art that various changes and modifications can be made therein without departing from the spirit and scope thereof.

What is claimed is:

1. A method for cultivating floating animal cells comprising introducing a culture medium into a cell culture unit comprising a shell and a plurality of hollow fibers enclosed in the shell, said hollow fibers being open at either end outside of the shell and having a pore diameter of from about 20 Å to $10^5$ Å, wherein the culture medium passes through the interior of the hollow fibers and floating animal cells are introduced and are cultivated in the space between the shell and the hollow fibers.

2. A method as in claim 1 wherein the pore diameter of the hollow fibers is from $10^2$ Å to $5 \times 10^4$ Å.

3. A method as in claim 1 or 2 wherein the hollow fibers are made of polysulfone or polyether sulfone.

4. A method as in claim 1 or 2 wherein the floating animal cells are medullary tumor cells, leukemic cells, lymphocytic cells, or medullary tumor cells obtained by cell fusion with spleen cells or lymphocytic cells.

5. A method as in claim 1 wherein the floating animal cells are medullary tumor cells obtained by cell fusion with spleen cells or lymphocytic cells.

6. A method as in claim 1 or 2 wherein the shell is made of silicone polymer, polybutadiene, or a silicone-polycarbonate copolymer.

7. A method as in claim 1 or 2 wherein the cell culture unit is connected to a culture medium reservoir by a tube made of silicone polymer, polybutadiene or a silicone-polycarbonate copolymer.

8. A method as in claim 1 or 2 wherein a silicone polymer adhesive is used as a fixing layer holding in place both ends of the hollow fiber.

9. A method as in claim 1 or 2 wherein the floating animal cells are implanted in the cell culture unit at an initial concentration of $10^5$ to $5 \times 10^6$ cell/ml.

10. A method as in claim 1 or 2 wherein the cell culture unit is placed in a carbon dioxide gas incubator in which the $CO_2$ concentration is from 5 to 10% by weight.

* * * * *